United States Patent [19]

Yensen

[11] Patent Number: 4,762,964

[45] Date of Patent: Aug. 9, 1988

[54] YENSEN 3A

[75] Inventor: Nicholas P. Yensen, Tucson, Ariz.

[73] Assignee: Salt Weeds, Tucson, Ariz.

[21] Appl. No.: 912,226

[22] Filed: Sep. 29, 1986

[51] Int. Cl.$^4$ .............................................. A01H 1/02
[52] U.S. Cl. ....................................................... 800/1
[58] Field of Search .............................. 800/1; Plt./89

Primary Examiner—Robert E. Bagwill
Attorney, Agent, or Firm—Cahill, Sutton & Thomas

[57] ABSTRACT

A non-grain variety, Yensen 3a, a variety of *Distichlis palmeri*, characterized by vigorous growth in salty soils, high pollen production and ideal height for pollination of grain producing variety Yensen 1a.

3 Claims, No Drawings

YENSEN 3A

BACKGROUND OF THE INVENTION

The present invention relates to a new and distinct variety of a plant of the family Poaceae and more particularly to a plant of the species *Distichlis palmeri* (Vasey) Fassett ex I. M. Johnston, commonly known as salt grass and is a perennial herbaceous flowering plant.

SUMMARY OF THE INVENTION

The new variety has a number of characteristics and desirable features distinguishing it as an improved variety. These characteristics are principally the vigorous growth, high pollen production and ideal height suitable for broadcast of pollen.

DESCRIPTION OF THE PREFERRED EMBODIMENTS

The new variety was noted in test plantings wherein approximately 100,000 seeds, seedlings and cuttings have been test planted under agricultural conditions on a total of 2.5 acres following over ten (10) years of study of salt-tolerant plants. The purpose of these large plantings was specifically to discover new varieties with crop potential and to learn their agronomic requirements. The new variety resulted from a bed seedling.

The new variety was first noted for its vigorous growth and ideal form and later for its high yield of pollen on relatively long stalks. The stalks are erect and the flower spikes are of a suitable height for broadcasting pollen.

The new variety is being reproduced via rhizomes in Tucson, Ariz., where a number of other varieties are also being observed.

The following is a detailed description of the new variety:

Parentage: A seedling from a harvested caryopses (seeds) of *Distichlis palmeri*. The harvested caryopses from which the Yensen 1a variety emerged were among literally millions of harvested caryopses which were then selected for size and weight. While approximately 100,000 caryopses have been so selected and test planted, the particular test planting from which Yensen 1a emerged had approximately 3,000 caryopses. This test planting was in plot number 2 ... of 9 test plots planted at Tucson, Ariz. These test plots were subjected to various stresses, e.g. water, temperature, salts, etc. such that only 0.1% to 1% of the caryopses reached maturity. The plants that survive this rigorous selection process are often phenotypically similar. This may be true in part due to similar genetic combinations that can survive the same rigorous selection process, and in part to the harvested caryopses being frequently derived from a few phenotypically similar parents. Due to (1) the nature of the selection process wherein massive numbers of caryopses are utilized, and (2) the heavy selection pressures, it is not practical to follow individual caryopses and their lineages.

Propagation: To date all rhizomes, shoots, and tillers have held true to the distinguishing characteristics of the initial plants and it is expected that at least 90% of the male plants from caryopses will be phenotypically similar to the distinguishing characteristics of the initial plants as they are described herein.

Culms: Rigid, erect, occasionally branched, glabrous, 35–60 cm high, 2–3 mm in diameter. The color of the Yensen 3a variety is not significantly different from other varieties.

Rhizomes: Thick and scaled at nodes.

Blades: Firm, rigid, ascending, pointed and pungent, involute (especially upon drying), distichous, glabrous to slightly puberulent, 3–4 mm basal width, 20–30 veins at base, typically 25–70 mm in length.

Sheath: Glabrous to slightly puberulent, with a tuft of wooly hairs at either side of the mouth, ligule smooth with pubescence apically.

Inflorescence:
  Panicle—erect, compoundly branched (often branched in two's), 6–10 cm in length and does not extend beyond the leaves.
  Spikelet—with 4–8 flowers, subtending "bracts" infertile, 10–20 mm in length, 3-mm in width.
  Florets
  lemma 6–10 mm in length decreasing slightly apically on the spikelet, 4–6 nerves on either side of a low keel;
  palea 5–7 mm in length, length decreasing slightly apically on the spikelet.
  Anther—3–5 mm in length, length decreasing slightly apically on the spikelet, 0.5–1.0 mm in width, approximately 1 mm in height; consisting of two (2) bilobed pollen sacks with midrib extending from ca. the first ¼ to ½ of the anther length with the remainder of the pollen sacks free, the free lobes more attenuated distally than medially; filament attached to and continuous with midrib.
  Pollen—20–40 microns in diameter, spherical, light yellow.

I claim:

1. A new and distinct plant variety, Yensen 3a, of *Distichlis palmeri*, which is principally characterized by vigorous growth, high pollen production and ideal height for pollination.

2. Plant material of plant variety of claim 1 selected from the group consisting of pollen, cuttings and rhizomes.

3. A new and distinct plant variety, Yensen 3a, which is principally distinguished by culms 35–60 cm in height, 2–3 mm in diameter; blades glabrous to slightly puberulent with 3–4 mm basal width and 20–30 veins at base, typically 25–70 mm in length; sheath glabrous to slightly puberulent; ligule smooth with pubescence apically; spikelet 10–20 mm in length and 3–4 mm wide; lemma 6–10 mm in length, decreasing slightly apically on the spikelet, 4–6 nerves on either side of a low keel; anther 3–5 mm in length, length decreasing slightly apically on the spikelet, 0.5–1.0 mm in width, approximately 1 mm in height; consisting of two (2) bilobed pollen sacks with midrib extending from ca. the first ¼ to ½ of the anther length with the remainder of the pollen sacks free, the free lobes more attenuated distally than medially; filament attached to and continuous with midrib; Pollen 20–40 microns in diameter, spherical, light yellow.

* * * * *